United States Patent
Bristow

(10) Patent No.: US 10,005,754 B2
(45) Date of Patent: Jun. 26, 2018

(54) FORM OF SPIRODICLOFEN, A PROCESS FOR ITS PREPARATION AND USE THE SAME

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 119 days.

(21) Appl. No.: 14/967,950

(22) Filed: Dec. 14, 2015

(65) Prior Publication Data

US 2017/0166546 A1    Jun. 15, 2017

(51) Int. Cl.

| | |
|---|---|
| *A01N 43/12* | (2006.01) |
| *A01N 43/26* | (2006.01) |
| *A61K 31/34* | (2006.01) |
| *A61K 31/335* | (2006.01) |
| *C07D 307/94* | (2006.01) |
| *A01N 25/04* | (2006.01) |

(52) U.S. Cl.
CPC .......... *C07D 307/94* (2013.01); *A01N 25/04* (2013.01); *A01N 43/12* (2013.01); *C07B 2200/13* (2013.01)

(58) Field of Classification Search
None
See application file for complete search history.

(56) References Cited

U.S. PATENT DOCUMENTS 5,262,383 A    11/1993    Fischer et al.

OTHER PUBLICATIONS

McClurg, "X-Ray Powder Diffraction (XRPD) to Describe Crystal Forms," Jul. 9, 2008.*

* cited by examiner

*Primary Examiner* — Jared D Barsky
(74) *Attorney, Agent, or Firm* — Dickinson Wright PLLC

(57) ABSTRACT

A new crystalline form of spirodiclofen of formula (I), the crystal preparation process, the analyzes of the crystal through various analytical methods and using the crystal to prepare stable agrochemical formulation. The invention also describes the use of various solvents towards the crystalline form preparation conditions.

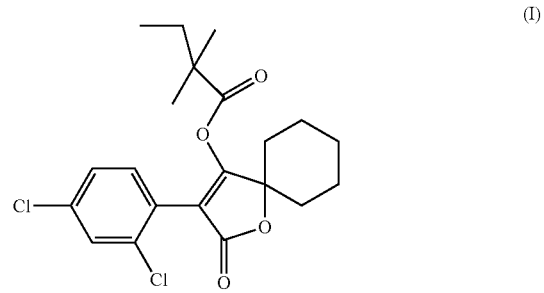

9 Claims, 4 Drawing Sheets

FORM OF SPIRODICLOFEN, A PROCESS FOR ITS PREPARATION AND USE THE SAME

BACKGROUND

Fields

The present disclosure relates to a crystalline form of 3-(2,4-dichlorophenyl)-2-oxo-1-oxaspiro[4.5]dec-3-en-4-yl-2,2-dimethyl butyrate (spirodiclofen), to its preparation processes and to its use in agrochemical preparations.

DESCRIPTION OF RELATED ART 3-(2,4-dichlorophenyl)-2-oxo-1-oxaspiro[4.5]dec-3-en-4-yl-2,2-dimethyl butyrate, having the common name of spirodiclofen, is a member of the ketoenol or tetronic acid class of chemicals. It is the first member of the ketoenol group with unique symptomology of poisoning and novel biochemical mode of action. It is used as non-systemic foliar insecticide and acaricide with a wide spectrum. Its pesticidal mode of action is through the inhibition of lipid synthesis by the inhibition of acetyl-CoA-carboxylase, which is a key enzyme in fatty acid biosynthesis. It controls the pests by interfering with mite development, pests such as *Panonychus* spp., *Phyllocoptruta* spp., *Brevipalpus* spp., *Aculus* spp. and *Tetranychus* spp. It controls mites and San Joe scales in citrus fruits, grapes, pome fruit, stone fruit, and tree nut crops.

Spirodiclofen has molecular formula of $C_{21}H_{24}Cl_2O_4$. Its chemical structure is

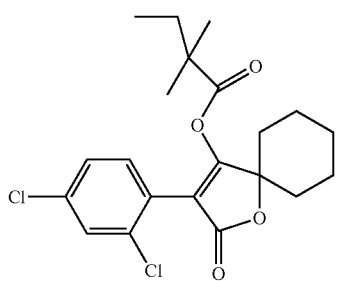

(I)

SUMMARY

The commercially available spirodiclofen, which is usually manufactured by the process described in U.S. Pat. No. 5,262,383A, which is incorporated herein by reference for all purposes, is present in an amorphous state having a melting point of 85° C. to 87° C. It has been found that spirodiclofen in amorphous state is not suitable for being prepared as compositions or formulations due to its high tendency of aggregation after prolong storage. Therefore, there is a need to develop a novel form of spirodiclofen exhibiting an improved storage stability.

Accordingly, an embodiment of the invention provides a novel crystalline form of spirodiclofen, termed "crystalline modification I", and a process for its preparation, as well as agrochemical compositions containing it, and methods for using it in agrochemical applications, such as methods for applying it to plants, surroundings, and plant parts. The novel crystalline modification I has been advantageously found to have improved storage stability with significant reduction in aggregation after prolong storage.

Accordingly, an embodiment of the invention also provides compositions for controlling undesirable pests, such as mite pests, comprising the crystalline modification I of spirodiclofen on its own, as a mixture with auxiliaries and carriers, and as a mixture with other active compounds. The use of the crystalline modification I of spirodiclofen in the control of undesirable pests and a method for the same are also provided by an embodiment of the invention.

BRIEF DESCRIPTION OF DRAWINGS

Various features and aspects of the embodiments of the invention disclosed herein can be more clearly understood by reference to the drawings, which are intended to exemplify and illustrate, but not to limit, the scope of the invention, and wherein.

DETAILED DESCRIPTION OF SPECIFIC EMBODIMENTS

The invention can be more clearly understood by reference to the following detailed description of specific embodiments thereof, which is intended to illustrate, but not limit, the scope of the appended claims.

It has been found that the present crystalline modification I of spirodiclofen has a significant improvement in its stability without aggregation formed after prolong storage. In addition, it is found that the crystalline modification I of spirodiclofen is easier to filter, comminute and/or grind compared to amorphous spirodiclofen prepared in accordance with the disclosure of U.S. Pat. No. 5,262,383. This allows the preparation of commercial formulations such as suspension concentrates (SC), oil-based suspension concentrates (OD), water-dispersible granules (WG) and water-soluble granules (SG). By virtue of its high storage stability, the crystalline modification I of spirodiclofen gives the desired long storage period to its formulations. Hence, it is possible to prepare any formulations of spirodiclofen in crystalline modification I, which is disclosed hereinafter.

According to an embodiment of the invention, a crystalline modification I of spirodiclofen is provided, exhibiting at least 3 of the following reflexes, in any combination, as 2θ values in an X-ray powder diffractogram recorded using Cu-Kα radiation at 25° C.:

$2\theta = 11.322 \pm 0.2$ (1)

$2\theta = 14.858 \pm 0.2$ (2)

$2\theta = 15.382 \pm 0.2$ (3)

$2\theta = 17.184 \pm 0.2$ (4)

$2\theta = 19.617 \pm 0.2$ (5)

$2\theta = 21.739 \pm 0.2$ (6)

$2\theta = 22.784 \pm 0.2$ (7)

$2\theta=23.840\pm0.2$ (8)

$2\theta=25.725\pm0.2$ (9)

$2\theta=28.195\pm0.2$ (10)

$2\theta=30.974\pm0.2$ (11)

Figure 2:
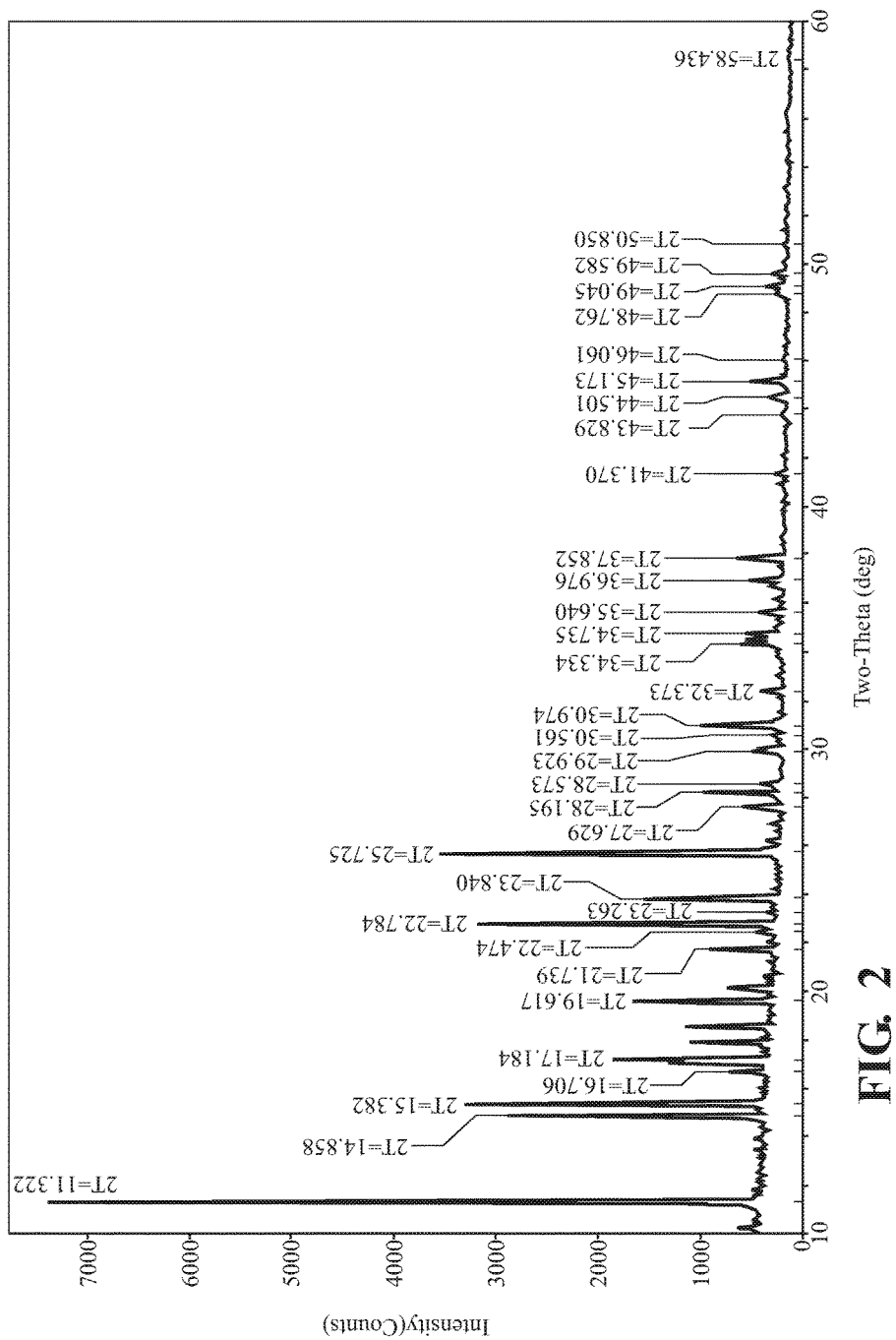
FIG. 2 is a X-ray powder diffractogram of an embodiment of crystalline modification I of spirodiclofen.

The crystalline modification I of spirodiclofen of an embodiment of the invention is characterized by an X-ray powder diffractogram having at least three of the reflexes indicated above, in any combination thereof. Preferably, the crystalline modification I is one having at least four of the aforementioned reflexes, more preferably at least five six or seven, or eight of said reflexes, again in any combination thereof. An X-ray powder diffractogram of the crystalline modification I of spirodiclofen is shown in FIG. 2, which will be described in detail hereinafter.

According to a preferred embodiment the crystalline modification I exhibits at least 3, 4, or 5 or all of the reflexes, in any combination, from the following:

$2\theta=11.322\pm0.2$ (1)

$2\theta=14.858\pm0.2$ (2)

$2\theta=15.382\pm0.2$ (3)

$2\theta=17.184\pm0.2$ (4)

$2\theta=19.617\pm0.2$ (5)

$2\theta=22.784\pm0.2$ (7)

$2\theta=23.840\pm0.2$ (8)

$2\theta=25.725\pm0.2$ (9)

The X-ray diffractogram was determined using powder diffractometer in reflection geometry in the range from 3-60° with increments of 0.03° using Cu-Ka radiation at 25° C.:

In a particularly preferred embodiment, the crystalline modification I of spirodiclofen displays a X-ray powder diffraction pattern substantially the same as shown in FIG. 2.

Figure 1:
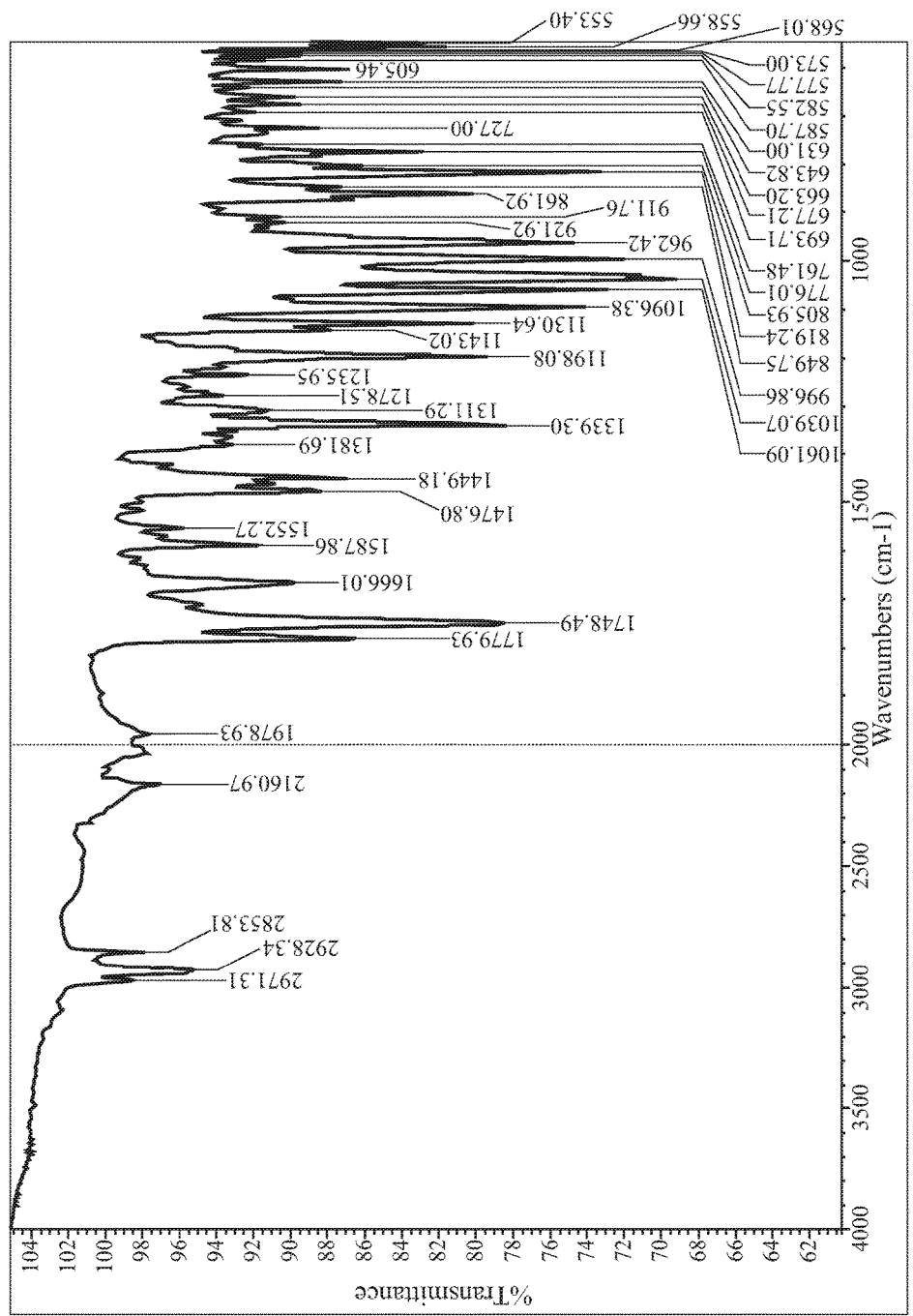
FIG. 1 is an infrared (IR) spectra of an embodiment of crystalline modification I of spirodiclofen.

In addition to the X-ray powder diffraction analysis, crystalline modification I of spirodiclofen can also be characterized by IR spectroscopy. The IR spectrum was measured with the resolution of 4 cm$^{-1}$ and with the number of scans of 16 for the purified sample. The crystalline modification I of spirodiclofen can be identified by the characteristic functional group vibrations peaks at wavenumbers (cm$^{-1}$, ±0.2%) of one or more of about 2971, 2928, 2854, 1780, 1749, 1096, 1061, 862, and 819 cm$^{-1}$, as shown in FIG. 1.

All IR spectra were obtained using the following acquisition parameters:

| | |
|---|---|
| FT-IR spectrometer | Bruker Tensor 37 |
| Diamond ATR unit | from Specac |
| Wavelength range | 550-4000 cm$^{-1}$ |
| Resolution | 4 cm$^{-1}$ |
| Number of scans | 16 |

Figure 3:
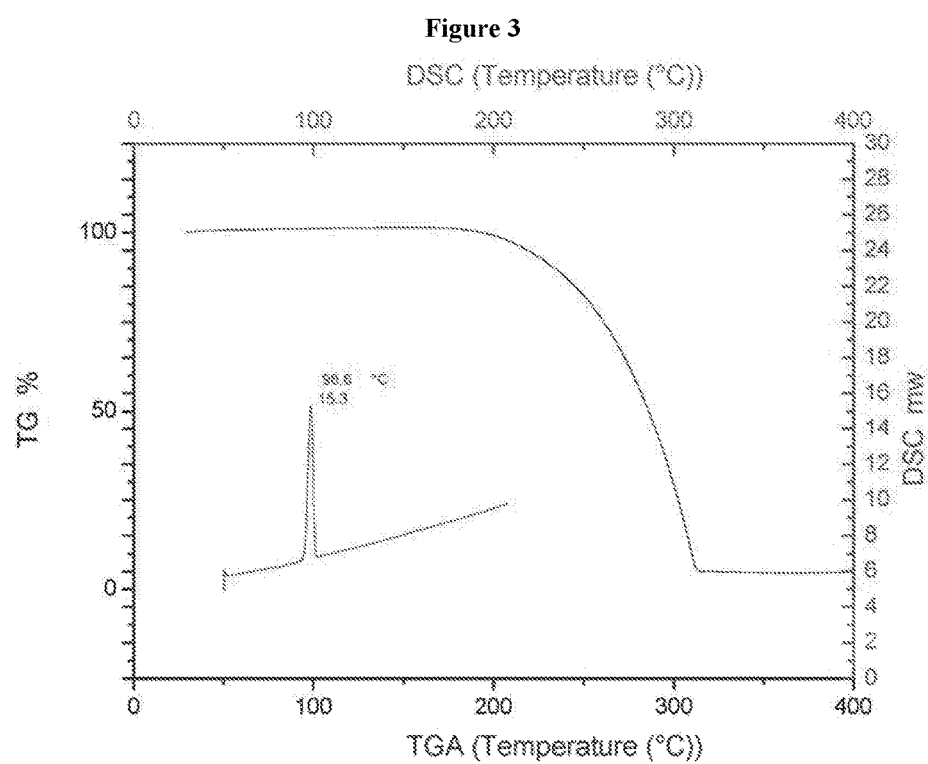
FIG. 3 is a Differential Scanning Calorimetry (DSC) thermogram of an embodiment of crystalline modification I of spirodiclofen.
Figure 4:
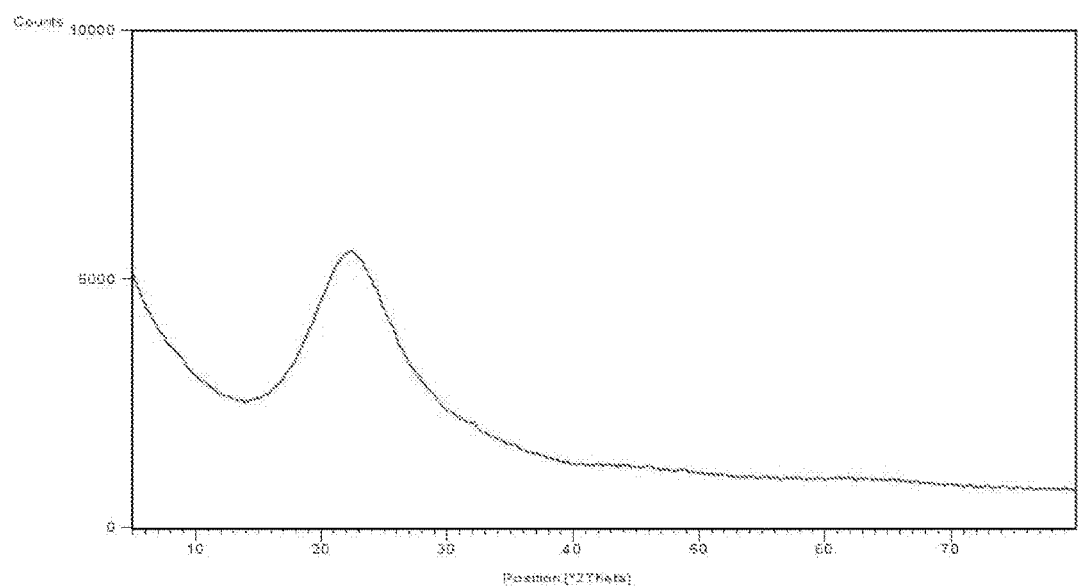
FIG. 4 is a X-ray powder diffractogram of amorphous spirodiclofen.

The crystalline modification I of spirodiclofen according to an embodiment of the invention may be further characterized by Differential Scanning Calorimetry (DSC) (FIG. 3). An endothermic peak at about 98.6° C. is shown in FIG. 3. As used herein, the terms "about 98.6° C." refers a range of 96° C. to 100° C.

Methods for preparing amorphous spirodiclofen are known in the art. Amorphous spirodiclofen is manufactured and available on a commercial scale. A particularly suitable method for preparing amorphous spirodiclofen is described in U.S. Pat. No. 5,262,383.

According to an embodiment of the invention, the crystalline modification I of spirodiclofen can be obtained by the processes below:

Spirodiclofen in the amorphous state is dissolved and then crystallized from a solvent.

In one aspect, an embodiment of the invention provides a process for preparing a crystalline modification I of spirodiclofen comprising steps of:

i) dissolving an amorphous spirodiclofen in a solvent;
ii) precipitating the dissolved compound into crystalline modification I of spirodiclofen of formula I; and
iii) isolating the precipitated crystalline modification I.

Suitable solvents for preparation of spirodiclofen crystalline modification I include: halogenated hydrocarbons (for example, chlorobenzene, bromobenzene, dichlorobenzene, chlorotoluene, trifluoro methyl benzene and trichlorobenzene), ethers (for example, diethyl ether, ethyl propyl ether, n-butyl ether, anisole, phenetole, cyclohexyl methyl ether, dimethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyltetrahydrofuran, polyethers of ethylene oxide and/or propylene oxide), nitrated hydrocarbons (for example, acetonitrile, nitromethane, nitroethane, nitropropane, nitrobenzene, chloronitrobenzene, ethyl benzene and o-nitrotoluene), aromatic hydrocarbons (cymene, petroleum fractions having a boiling range of from 70° C. to 190° C., petroleum ether, ligroin, mesitylene, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), and ketone (for example, methyl ether ketone, acetone) and mixtures thereof.

Preferred solvents include toluene, xylene, benzene, chlorobenzene, dichlorobenzene, ethyl benzene, trifluoro methyl benzene, mesitylene, nitrobenzene, ether, methyl ethyl ketone, acetone and acetonitrile. Solvent mixtures of more than 2 or 3 or 4 components are also envisaged by embodiments of the invention.

In an embodiment of the invention, it is preferred that the solvents are aromatic hydrocarbons, which can be optionally substituted with one or more substituents, which may be the same or different, selected from the group consisting of alkyl groups, for example lower alkyl groups, for example $C_1$ to $C_4$ alkyl groups, which may optionally be further substituted with one or more halogens, which may be the same or different, nitro, and halogen, and ketones.

In an embodiment of the invention, it is preferred that the solvents are toluene and acetone.

Hence, according to a preferred embodiment in step (i), amorphous spirodiclofen is dissolved in a solvent comprising toluene or acetone. In a preferred embodiment, the solvent essentially consists of toluene and/or acetone.

According to an embodiment of in step (i), amorphous spirodiclofen is dissolved in a solvent or a solvent mixture as a concentrated solution by heating from room temperature or ambient temperature to reflux temperature or below the reflux temperature of the solvent or the solvent mixture. Preferably, the concentrated solutions can be prepared at the reflux temperature of the solvents. The concentration of the solution depends on the solubility of spirodiclofen in the corresponding solvent or solvent mixture.

The concentrated homogeneous solution thus prepared as in step (i) is then cooled to room temperature or to a temperature of around 0° C. to 20° C. to crystallize the desired crystalline from the solvent. The crystalline modification I of spirodiclofen can also be crystallized out by concentrating the homogeneous solution by removing the solvent or solvent mixture to certain volume with or without applying vacuum and cooling to below the reflux temperature of the solvent or the solvent mixture.

In another embodiment, crystalline modification I of spirodiclofen can also be effected by adding seed crystals of the desired crystalline form during crystallization into a solution prepared in step (i), which can promote or accelerate the crystallization.

The seed crystal amount added to the concentrated solution is typically in the range of 0.001% to 5% by weight, often 0.005% to 0.5% by weight based on the weight of spirodiclofen used for the preparation of concentrated solution in step (i). Preferably, the seed crystals are added to the concentrated solution at the temperature below the boiling point of the corresponding solvent or the solvent mixture.

Hence, the precipitation of the crystalline form I of spirodiclofen can be effectively achieved from the concentrated solution by a person of ordinary skill in the art.

The precipitated crystalline modification I of spirodiclofen obtained from step (ii) is isolated by the usual solid component separating techniques from solutions, such as filtration, centrifugation or decantation. Then, the isolated solid precipitate is washed with solvent one or more times. Preferably, the solvent employed in the washing stage consists of one or more components of the solvent or solvent mixture employed for preparation of concentrated solution in step (i), as described hereinbefore. The washing is usually carried out using the corresponding solvent or solvent mixture between room temperature and 0° C., depending on the solubility of the crystal, in order to minimize or avoid the loss of crystalline material in the corresponding washing solvent as much as possible.

The invention, in an embodiment, also relates to a composition comprising the crystalline modification I of spirodiclofen. The amount of the crystalline modification I of spirodiclofen is less than 75% by weight of the composition, preferably less than 50% by weight of the composition, more preferably less than 30% by weight of the composition, still more preferably about 25% by weight of the composition.

The use of amorphous spirodiclofen as an insecticide and/or acaricide is known in the art and is used on a commercial scale. The crystalline modification I of spirodiclofen is also active in controlling undesirable pests, such as mites, for example, as disclosed in the documents described hereinbefore. Spirodiclofen in the crystalline modification I of the present invention may be formulated and applied in manner analogous to those described for amorphous spirodiclofen.

Accordingly, in a further aspect, an embodiment of the invention provides an insecticidal composition comprising spirodiclofen in the crystalline modification I as defined hereinbefore.

Accordingly, an embodiment of the invention furthermore provides processes for preparing compositions for controlling undesirable pests, such as mites using the crystalline modification I of spirodiclofen.

Accordingly, the invention also provides a method for controlling undesirable pests in plants, plant parts, and/or their surroundings, comprising applying to the foliage or fruit of the plant, plant parts, or surroundings of the plant, an insecticidally effective amount of crystalline modification I of spirodiclofen.

The crystalline modification I of spirodiclofen can be incorporated into the customary formulations, such as suspension concentrates (SC), oil-based suspension concentrates (OD), water-soluble granules (SG), dispersible concentrates (DC), emulsifiable concentrates (EC), emulsion seed dressings, suspension seed dressings, granules (GR), microgranules (MG), suspoemulsions (SE) and water-dispersible granules (WG) using suitable auxiliaries, carriers and solvents, in a manner analogous to that known for amorphous spirodiclofen.

In this context, the crystalline modification I of spirodiclofen may be present in a concentration of from about 0.1% to about 75% by weight of the total mixture, i.e., in amounts sufficient to achieve the required dosage. The formulations are prepared, for example, by extending the crystalline modification I of spirodiclofen with water, solvents and carriers, using, if appropriate, emulsifiers and/or dispersants, and/or other auxiliaries.

These formulations are prepared by mixing the crystalline modification I of spirodiclofen with at least one insecticidally acceptable auxiliaries, for example, surfactants, liquid diluents, solid diluents, wetting agents, dispersants, thickening agents, antifoaming agents, anti-freezing agents, preservatives, antioxidants, solid adherents, inert fillers and other formulation ingredients.

Surfactants can be an emulsifier, dispersant or wetting agent of ionic or nonionic type. Examples which may be used include, but are not limited to, salts of polyacrylic acids, salts of lignosulphonic acid, salts of phenylsulphonic or naphthalenesulphonic acids, polycondensates of ethylene oxide with fatty alcohols or with fatty acids or with fatty amines, substituted phenols, especially alkylphenols, sulphosuccinic ester salts, taurine derivatives, especially alkyltaurates, or phosphoric esters of polyethoxylated phenols or alcohols.

Liquid diluents include, but are not limited to, water, N,N-dimethylmamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetine, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such methanol, cyclohexanol, decanol, benzyl and tetrahydrofurfuryl alcohol, and mixtures thereof.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol. Examples of water-insoluble solid diluents include, but are not limited to clays, synthetic and diatomaceous silicas, calcium and magnesium silicates, titanium dioxide, aluminum, calcium and zinc oxide, and mixtures thereof.

Wetting agents include, but are not limited to, alkyl sulfosuccinates, laureates, alkyl sulfates, phosphate esters, acetylenic diols, ethoxyfluornated alcohols, ethoxylated silicones, alkyl phenol ethyoxylates, benzene sulfonates, alkyl-substituted benzene sulfonates, alkyl a-olefin sulfonates, naphthalene sulfonates, alkyl-substituted napthalene sulfonates, condensates of naphthalene sulfonates and alkyl-substituted naphthalene sulfonates with formaldehyde, and alcohol ethoxylates, and mixtures thereof. Alkyl naphthalene sulphonates, sodium salts are particularly useful for the composition of the invention Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates. Ligninsulfonates such as sodium ligninsulfonates are particularly useful for the composition of the invention. Naphthalene sulfonate-formaldehyde condensates such as Naphthalenesulfonic acid, polymers with formaldehyde, and sodium salts are particularly useful for the composition of the invention Thickening agents include, but are not limited to, guar gum, pectin, casein, carrageenan, xanthan gum, alginates, methylcellulose, hydroxyethylcellulose, hydroxypropylcellulose, and carboxymethylcellulose, and mixtures thereof. Synthetic thickening agents include derivatives of the former categories, and also polyvinyl alcohols, polyacrylamides, polyvinylpyrrolidones, various polyethers, their copolymers as well as polyacrylic acids and their salts, and mixtures thereof. Alkylpolyvinylpyrrolidones are particularly useful for the composition of the invention.

Antifoaming agents include all substances which can normally be used for this purpose in agrochemical compositions. Suitable antifoaming agents are known in the art and are available commercially. Particularly preferred antifoam agents are mixtures of polydimethylsiloxanes and perfluroalkylphosphonic acids, such as the silicone antifoaming agents available from GE or Compton.

Preservatives include all substances which can normally be used for this purpose in agrochemical compositions of this type and again are well known in the art. Suitable examples that may be mentioned include PREVENTOL® (from Bayer AG) and PROXEL® (from Bayer AG).

Antioxidants include all substances which can normally be used for this purpose in agrochemical compositions, as is known in the art. Preference is given to butylated hydroxytoluene.

Solid adherents include organic adhesives, including tackifiers, such as celluloses or substituted celluloses, natural and synthetic polymers in the form of powders, granules, or lattices, and inorganic adhesives such as gypsum, silica or cement.

Inert fillers include but are not limited to, natural ground minerals, such as kaolins, aluminas, talc, chalk, quartz, attapulgite, montmorillonite, and diatomaceous earth, or synthetic ground minerals, such as highly dispersed silicic acid, aluminum oxide, silicates, and calcium phosphates and calcium hydrogen phosphates. Suitable inert fillers for granules include, for example, crushed and fractionated natural minerals, such as calcite, marble, pumice, sepiolite, and dolomite, or synthetic granules of inorganic and organic ground materials, as well as granules of organic materials, such as sawdust, coconut husks, corn cobs, and tobacco stalks.

Other formulation ingredients can also be used in the present invention such as dyes, drying agents, and the like. These ingredients are known to one skilled in the art.

The crystalline modification I of spirodiclofen according to an embodiment of the invention can be present in formulations and in other forms that are prepared from these formulations, and as a mixture with other active compounds (such as attractants, sterilizing agents, bactericides, acaricides, nematicides, fungicides, growth-regulating substances, herbicides, safeners, fertilizers, semiochemicals and other insecticides) or with agents for improving plant properties.

When used as insecticide or acaricide, the crystalline modification I of spirodiclofen according to an embodiment of the invention can furthermore be present in formulations and in other forms, prepared from these formulations, and as a mixture with inhibitors which reduce degradation of the active compounds after their use in the environment of the plant, on the surface of plant parts, or in plant tissues.

All plants, plant parts and their surroundings can be treated with the crystalline modification I of spirodiclofen in accordance with an embodiment of the invention. In the present context, plants are to be understood as meaning all plants and plant populations, such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoots, leaves, needles, stalks, stems, flowers, fruit bodies, fruits, seeds, roots, tubers and rhizomes. Harvested materials, and vegetative and generative propagation materials, for example, cuttings, tubers, meristem tissues, rhizomes, offsets, seeds, single and multiple plant cells, and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

As used herein the term "room temperature" refers to a temperature range of from about 20° C.-26° C.

"Surrounding," as used herein, refers to the place on which the plants are growing, the place on which the plant propagation materials of the plants are sown or the place on which the plant propagation materials of the plants will be sown.

Treatment according to the invention of the plants and plant parts with the compositions or formulations of the inventions is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

The benefits of the invention are seen most when the insecticidal composition is applied to kill pests, such as mites in growing crops of useful plants: such as maize (corn) including field corns, pop corns and sweet corns, cotton, cereal, barley, wheat, rice, oats, potatoes, sugar beets, plantation crops (such as bananas, fruit trees, rubber trees, tree nurseries), tree nut crops, grapes, citrus fruit, pome fruit, stone fruit, olive, amenity, asparagus, bushberries (such as blueberries), caneberries, cranberries, flax, grain sorghum, okra, peppermint, rhubarb, spearmint, turf grass, and sugarcane. In this invention, treatment of citrus fruits, grapes, pome fruit, stone fruit, and tree nut crops are particularly beneficial.

All percentages are given in weight % unless otherwise indicated.

Embodiments of the invention will now be described by way of the following examples, which are provided for illustrative purposes only, and not intended to limit the scope of the disclosure.

EXAMPLES

Example 1: Preparation of Amorphous Spirodiclofen in Accordance with the Disclosure of U.S. Pat. No. 5,262,383 with Modification 1. Preparation of Hexylester: Example 1a with Modification (Column 125)

0.1 mol of ethyl-1-hydroxycyclohexanecarboxylate were introduced into 200 ml of absolute methylene dichloride, 0.12 mol of triethylamine (Et₃N) were added, and a solution of 0.1 mol of 2-(2,4-dichlorophenyl)acetyl chloride in 50 ml of absolute methylene dichloride was added dropwise at 0-10° C.

After the solution had been stirred for 16 h at room temperature, it was washed with aqueous citric acid and aqueous sodium bicarbonate solution, and the organic phase was dried over sodium sulfate and evaporated on a rotary evaporation.

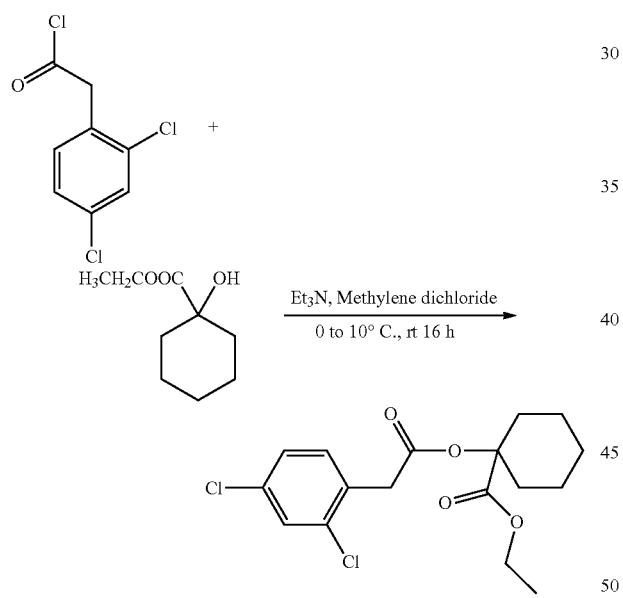

2. Preparation of 3-(2,4,-dichlorophenyl)-4-hydroxy-5-cyclohexane-3-dihydrofuran-2-one: Example 1a-2 with modification (column 90)

90 mmol of sodium hydride (80%) were introduced into 50 ml of absolute toluene. This procedure was carried out under an Argon-Atmosphere. The mixture was heated to reflux temperature. 60 mmol of hexylester dissolved in 70 ml of absolute toluene were then added dropwise under reflux conditions, and the mixture is refluxed for 3 hours.

The solution was evaporated on a rotary evaporator, the residue was taken up in water, and the solution was acidified. The precipitate which separated out during this process was taken up in methylene chloride, and the aqueous mother liquor was extracted repeatedly. The extract was subsequently dried over sodium sulfate and concentrated on a rotary evaporator.

The product was suspended in 20 ml of hot chloroform, 60 ml of n-hexane were slowly added under reflux conditions, the mixture was allowed to cool slowly, and solids were filtered off with suction and dried.

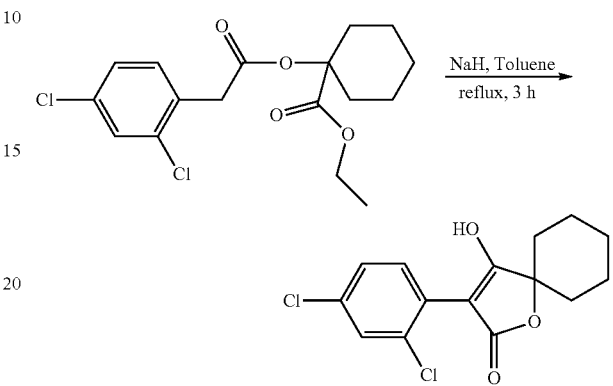

3. Preparation of Spirodiclofen: Example 1 b-1 with Modification (Column 95)

5 mmol of 3-(2,4,-dichlorophenyl)-4-hydroxy-5-cyclohexane-3-dihydrofuran-2-one were introduced into 20 ml of absolute methylene dichloride. To this mixture, there was added 6 mmol of trimethylamine (Et₃N), a solution of 6 mmol of 2,2-dimethylbutyryl chloride in 5 ml absolute methylene chloride was added at 0-10° C. and stirring was continued for 1 hour at room temperature.

The solution was washed with aqueous citric acid and aqueous sodium hydrogen carbonate solution, dried over sodium sulfate and evaporated by rotary evaporation.

Scheme 1. Synthesis of Spirodiclofen

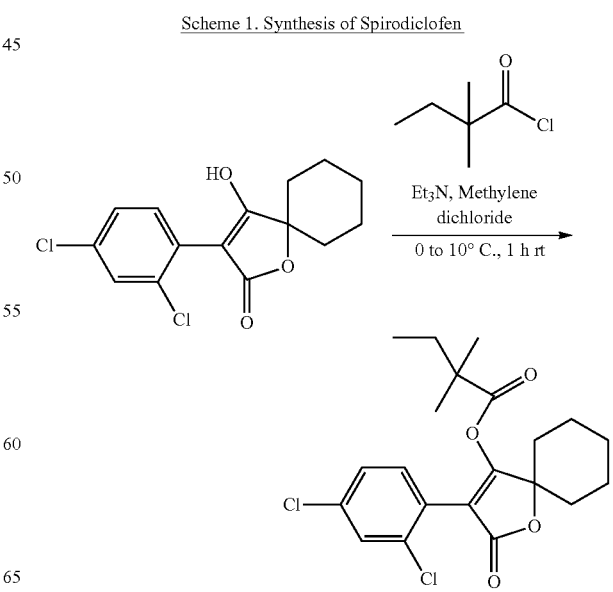

Preparation of Crystalline Modification I of Spirodiclofen

Example 2—Crystallization from Toluene

Amorphous spirodiclofen sample (10 g) as prepared in Example 1 was taken in a 3-neck round bottom flask along with toluene (70 mL). The resulting slurry was heated to 90° C. to get a homogeneous solution. The homogeneous solution was filtered to remove the insoluble particles, if any, and the filtered solution was slowly cooled down to room temperature (rt). Fine crystals were formed upon cooling and the resulting heterogeneous mixture was stirred at rt for 2 h. Then, the slurry was filtered and washed with toluene (3 mL). The filtered crystals were dried under vacuum at 60° C. in order to remove the toluene traces from the crystalline product. The crystalline product thus obtained was having a purity of 98%. The yield of the recovered product as crystal was found to be 85%.

The obtained crystal was analyzed by IR, powder X-ray and DSC analyses and found out to be crystalline modification I of spirodiclofen as shown in in FIGS. 1, 2 and 3, respectively.

The differential scanning calorimetry (DSC) thermogram (FIG. 3) shows an endothermic melting peak at about 98.6° C.

The IR spectrum of spirodiclofen shows the functional group characteristic vibrations peaks at wavenumbers (cm$^{-1}$, ±0.2%) of one or more of about 2971, 2928, 2854, 1780, 1749, 1096, 1061, 862, and 819 cm$^{-1}$ in FIG. 1.

The X-ray powder diffractogram of crystals showed the reflexes in FIG. 2 and the values are summarized in Table 1.

TABLE 1

X-ray powder diffractogram reflexes of crystalline modification I of Spirodiclofen
Crystalline Modification

| 2 θ (°) | d (Å) |
|---|---|
| 11.322 ± 0.2 | 9.07 ± 0.05 |
| 14.858 ± 0.2 | 6.92 ± 0.05 |
| 15.382 ± 0.2 | 6.68 ± 0.05 |
| 16.706 ± 0.2 | 6.16 ± 0.05 |
| 17.184 ± 0.2 | 5.99 ± 0.05 |
| 19.617 ± 0.2 | 5.25 ± 0.05 |
| 21.739 ± 0.2 | 4.74 ± 0.05 |
| 22.474 ± 0.2 | 4.59 ± 0.05 |
| 22.784 ± 0.2 | 4.53 ± 0.05 |
| 23.840 ± 0.2 | 4.33 ± 0.05 |
| 25.725 ± 0.2 | 4.02 ± 0.05 |
| 27.629 ± 0.2 | 3.75 ± 0.05 |
| 28.195 ± 0.2 | 3.67 ± 0.05 |
| 28.573 ± 0.2 | 3.63 ± 0.05 |
| 29.923 ± 0.2 | 3.47 ± 0.05 |
| 32.373 ± 0.2 | 3.21 ± 0.05 |
| 34.334 ± 0.2 | 3.03 ± 0.05 |
| 34.735 ± 0.2 | 3.00 ± 0.05 |
| 35.640 ± 0.2 | 2.92 ± 0.05 |
| 36.976 ± 0.2 | 2.82 ± 0.05 |
| 37.852 ± 0.2 | 2.76 ± 0.05 |
| 44.501 ± 0.2 | 2.36 ± 0.05 |
| 45.173 ± 0.2 | 2.33 ± 0.05 |
| 49.045 ± 0.2 | 2.16 ± 0.05 |

Example 3—Crystallization from Acetone

Spirodiclofen (5 g) sample prepared in Example 1 was taken in a 3-neck round bottom flask along with acetone (35 mL) and the resulting slurry was heated to reflux to get a homogeneous solution. The resultant hot solution was filtered to remove the insoluble (if any) and the resulting filtered solution was slowly cooled to rt. Product was precipitated out as fine crystal during cooling and the mixture was stirred at rt for 2 h. Then, the slurry was filtered, washed with acetone (3 mL) and dried under vacuum at 40° C. in order to remove the acetone traces from the crystal. The crystal thus obtained was having a purity of 98% and the recovered yield of the product was 85%.

The crystals were characterized as being spirodiclofen crystalline modification I using IR spectrometry, X-ray diffraction and DSC, as described in Example 2.

Example 4—Preparation of Amorphous Spirodiclofen SC

All the components list in Table 2 below were mixed uniformly and the resulting mixture was ground with a Dyno-Mill (manufactured by Willy A. Bachofen AG) to obtain a suspension concentrate.

TABLE 2

| Content | Weight % | Function |
|---|---|---|
| Amorphous spirodiclofen, 98% (prepared in Example 1) | 25.51 | Active ingredient |
| Sodium alkyl naphthalene sulfonate | 5 | Dispersing agent |
| Xanthan gum | 0.3 | Thickening agent |
| Propylene glycol | 10.00 | Anti-freezing agent |
| 1,2-Benzisothiazol-3(2H)-one (PROXEL ®) | 0.3 | Preservative |
| Water | Balance to 100 | Filler |

Example 5—Preparation of the Crystalline Modification I of Spirodiclofen SC

All the components list in Table 3 below were mixed uniformly and the resulting mixture was ground with a Dyno-Mill (manufactured by Willy A. Bachofen AG) to obtain a suspension concentrate.

TABLE 3

| Content | Weight % | Function |
|---|---|---|
| Spirodiclofen, crystalline modification I, 98% (prepared in example 2) | 25.51 | Active ingredient |
| Sodium alkyl naphthalene sulfonate | 5 | Dispersing agent |
| Xanthan gum | 0.3 | Thickening agent |
| Propylene glycol | 10.00 | Antifreeze |
| 1,2-Benzisothiazol-3(2H)-one (PROXEL ®) | 0.3 | Preservative |
| Water | Balance to 100 | Filler |

Example 6: Comparison of Storage Stability

Samples prepared in Examples 4 and 5 were stored at 54° C. for 1 month, 3 months and 6 months. The procedures are followed according to CIPAC MT 46.3. The concentration of spirodiclofen was measured at the end of each storage time by HPLC. The aggregation was measured by observation. The original concentration of spirodiclofen in each formulation was 25%. The results are listed in Table 4.

TABLE 4

| | 1 month | | 3 month | | 6 month | |
|---|---|---|---|---|---|---|
| Sample | Concentration of spirodiclofen (%) | Aggregation | Concentration of spirodiclofen (%) | Aggregation | Concentration of spirodiclofen (%) | Aggregation |
| Example 4 | 20 | + | 11 | +++ | 9 | +++++ |
| Example 5 | 25 | − | 25 | − | 24 | − |

Remark:
"+" means small amount of aggregation.
"+++++" means a lot of aggregation.
"−" means no aggregation.

The invention claimed is:

1. A crystalline modification I of spirodiclofen (3-(2,4-dichlorophenyl)-2-oxo-1-oxaspiro[4.5]dec-3-en-4-yl-2,2-dimethylbutyrate), exhibiting each of the following reflexes as 2θ values in an X-ray powder diffractogram recorded using Cu—Kα radiation at 25° C.:

$$2\theta = 11.322 \pm 0.2 \quad (1)$$

$$2\theta = 14.858 \pm 0.2 \quad (2)$$

$$2\theta = 15.382 \pm 0.2 \quad (3)$$

$$2\theta = 17.184 \pm 0.2 \quad (4)$$

$$2\theta = 19.617 \pm 0.2 \quad (5)$$

$$2\theta = 22.784 \pm 0.2 \quad (7)$$

$$2\theta = 23.840 \pm 0.2 \quad (8)$$

$$2\theta = 25.725 \pm 0.2 \quad (9).$$

2. The crystalline modification I of spirodiclofen according to claim 1, exhibiting each of the following reflexes in an X-ray powder diffractogram recorded using Cu—Kα radiation at 25° C.:

$$2\theta = 11.322 \pm 0.2 \quad (1)$$

$$2\theta = 14.858 \pm 0.2 \quad (2)$$

$$2\theta = 15.382 \pm 0.2 \quad (3)$$

$$2\theta = 17.184 \pm 0.2 \quad (4)$$

$$2\theta = 19.617 \pm 0.2 \quad (5)$$

$$2\theta = 21.739 \pm 0.2 \quad (6)$$

$$2\theta = 22.784 \pm 0.2 \quad (7)$$

$$2\theta = 23.840 \pm 0.2 \quad (8)$$

$$2\theta = 25.725 \pm 0.2 \quad (9)$$

$$2\theta = 28.195 \pm 0.2 \quad (10).$$

3. The crystalline modification I of spirodiclofen according to claim 1, exhibiting an IR spectrum with characteristic functional group vibrations peaks at wavenumbers (cm$^{-1}$, ±0.2%) of one or more of about 2971, 2928, 2854, 1780, 1749, 1096, 1061, 862, and 819 cm$^{-1}$.

4. The crystalline modification I of spirodiclofen according to claim 1 exhibiting a Differential Scanning calorimeter (DSC) thermogram having an endothermic melting peak with onset at about 98.6° C.

5. A crystalline material comprising the crystalline modification I of spirodiclofen according to claim 1, wherein the crystalline modification I of spirodiclofen is obtained using a solvent, the solvent is toluene, and the crystalline material having a content of the crystalline modification I of spirodiclofen of at least 98% by weight.

6. A composition comprising the crystalline modification I of spirodiclofen according to claim 1 and at least one auxiliary.

7. The composition according to claim 6, wherein the auxiliary is selected from the group consisting of a surfactant, a diluent, a wetting agent, a dispersant, a thickening agent, an antifoaming agent, an anti-freezing agent, a preservative, an antioxidant, a solid adherent, an inert filler and mixtures thereof.

8. The composition according to claim 6, in the form of a suspension concentrate (SC), an oil-based suspension concentrate (OD), a water-soluble granule (SG), a dispersible concentrate (DC), an emulsifiable concentrate (EC), an emulsion seed dressing, a suspension seed dressing, a granule (GR), a microgranule (MG), a suspoemulsion (SE) or a water-dispersible granule (WG).

9. The composition according to claim 8, in the form of a suspension concentrate (SC).

* * * * *